US011534253B2

(12) United States Patent
Woo et al.

(10) Patent No.: US 11,534,253 B2
(45) Date of Patent: Dec. 27, 2022

(54) INTERVENTIONAL PROCEDURE HANDLE UNIT, INTERVENTIONAL PROCEDURE MASTER DEVICE USING SAME, AND REMOTE INTERVENTIONAL PROCEDURE SYSTEM USING SAME

(71) Applicant: KOREA INSTITUTE OF MACHINERY & MATERIALS, Daejeon (KR)

(72) Inventors: Hyun-soo Woo, Daejeon (KR); Jang-ho Cho, Daegu (KR); Hyuk-jin Lee, Gyeongsan-si (KR); Ki-soo Jeong, Daegu (KR)

(73) Assignee: KOREA INSTITUTE OF MACHINERY & MATERIALS, Daejeon (KR)

( * ) Notice: Subject to any disclaimer, the term of this patent is extended or adjusted under 35 U.S.C. 154(b) by 1002 days.

(21) Appl. No.: 16/322,326

(22) PCT Filed: Jul. 31, 2017

(86) PCT No.: PCT/KR2017/008213
§ 371 (c)(1),
(2) Date: Jan. 31, 2019

(87) PCT Pub. No.: WO2018/074715
PCT Pub. Date: Apr. 26, 2018

(65) Prior Publication Data
US 2019/0192247 A1 Jun. 27, 2019

(30) Foreign Application Priority Data
Oct. 18, 2016 (KR) .................. 10-2016-0135334

(51) Int. Cl.
*A61B 34/00* (2016.01)
*A61B 34/37* (2016.01)
(Continued)

(52) U.S. Cl.
CPC .............. *A61B 34/37* (2016.02); *A61B 34/76* (2016.02); *A61B 90/11* (2016.02); *B25J 3/00* (2013.01);
(Continued)

(58) Field of Classification Search
CPC ... A61B 34/30; A61B 34/76; A61B 2034/724; A61B 90/11; A61B 2017/00367;
(Continued)

(56) References Cited

U.S. PATENT DOCUMENTS 6,821,282 B2  11/2004  Perry et al.
8,560,118 B2  10/2013  Greer et al.
(Continued)

FOREIGN PATENT DOCUMENTS

JP  3538639 B2  4/2004
JP  4430096 B2  12/2009
(Continued)

OTHER PUBLICATIONS

Hyun Soo Woo et al., "Physicians' Requirement Analysis Based Design of the Master Device Mechanism for Teleoperated Interventional Robotic System" Journal of Institute of Control, Robotics and Systems, 2016, pp. 603-609.
(Continued)

*Primary Examiner* — Eduardo C Robert
*Assistant Examiner* — Christina Negrellirodriguez
(74) *Attorney, Agent, or Firm* — Hauptman Ham, LLP

(57) ABSTRACT

In a handle unit for interventional procedure, a master device for interventional procedure, and a remote control interventional procedure system, the handle unit is gripped by an operator. The handle unit includes a gripper, a mode selection module and a linear motion module. The gripper is gripped by the operator. The mode selection module is equipped to the gripper, and selects one of motion modes
(Continued)

including a linear motion mode, a rotational motion mode and a plane motion mode. The needle linearly moves with one degree of freedom in the linear motion mode. The needle rotationally moves with two degrees of freedom in the rotational motion mode. The needle moves in a plane with two degrees of freedom in the plane motion mode. The linear motion module performs the linear motion of the needle based on the selection of the mode selection module, and is equipped to the gripper.

13 Claims, 7 Drawing Sheets

(51) Int. Cl.
    *B25J 3/00*     (2006.01)
    *B25J 13/06*     (2006.01)
    *A61B 90/11*     (2016.01)
    *B25J 13/08*     (2006.01)
    *A61B 17/34*     (2006.01)
    *A61B 17/00*     (2006.01)
    *A61B 18/00*     (2006.01)
    *A61B 90/00*     (2016.01)

(52) U.S. Cl.
    CPC .............. *B25J 13/06* (2013.01); *B25J 13/08* (2013.01); *A61B 17/3401* (2013.01); *A61B 17/3403* (2013.01); *A61B 2017/00398* (2013.01); *A61B 2017/00424* (2013.01); *A61B 2017/00862* (2013.01); *A61B 2017/3405* (2013.01); *A61B 2017/3409* (2013.01); *A61B 2018/00303* (2013.01); *A61B 2034/742* (2016.02); *A61B 2090/067* (2016.02)

(58) Field of Classification Search
    CPC ...... A61B 2018/00916; A61B 17/2909; A61B 17/2912; A61B 17/2923; B25J 3/00; A61F 2/9517
    USPC .......................................................... 606/53
    See application file for complete search history.

(56) References Cited

U.S. PATENT DOCUMENTS

2012/0265051 A1* 10/2012 Fischer .................. A61B 34/30
                                                           73/800
2013/0006268 A1     1/2013   Swarup et al.

FOREIGN PATENT DOCUMENTS

| KR | 10-0925102 B1 | 11/2009 |
|---|---|---|
| KR | 10-2013-0015437 A | 2/2013 |
| KR | 10-2013-0108091 A | 10/2013 |
| KR | 10-2015-0000232 A | 1/2015 |
| KR | 10-2015-0146413 A | 12/2015 |
| KR | 10-2016-0001916 A | 1/2016 |

OTHER PUBLICATIONS

Hyun Soo Woo et al., "Optimal Design of the Master Device Mechanism for Teleoperated Interventional Robotic System", Mar. 2016, pp. 201-202.

International Search Report dated Dec. 6, 2017, corresponding to International Application No. PCT/KR2017/008213 citing the above reference(s).

* cited by examiner

INTERVENTIONAL PROCEDURE HANDLE UNIT, INTERVENTIONAL PROCEDURE MASTER DEVICE USING SAME, AND REMOTE INTERVENTIONAL PROCEDURE SYSTEM USING SAME

CROSS REFERENCE TO RELATED APPLICATION

This present application is a national stage filing under 35 U.S.C § 371 of PCT application number PCT/KR2017/008213 filed on Jul. 31, 2017 which is based upon and claims the benefit of priority to Korean Patent Application No. 10-2016-0135334 filed on Oct. 18, 2016 respectively in the Korean Intellectual Property Office. The disclosures of the above-listed applications are hereby incorporated by reference herein in their entirety.

BACKGROUND

1. Field of Disclosure

The present disclosure of invention relates a handle unit for interventional procedure, a master device for interventional procedure using the same, and a remote control interventional procedure system using the master device, and more specifically the present disclosure of invention relates to a handle unit for interventional procedure, a master device for interventional procedure using the same, and a remote control interventional procedure system using the master device, transmitting a moving order of an operator to a slave robot and a needle driver, providing an haptic feedback on a limit of degrees of freedom on the operation proper to the interventional procedure and an information generated in the interventional procedure to the operator, in the remote control interventional procedure system developed for performing the interventional procedure with a remote control using a robot.

2. Description of Related Technology

Generally, in interventional procedure, an inside of human beings is monitored by an imaging device and a medical device is inserted into the inside thereof for an operation. The interventional procedure is a general medical technology used for the medical procedures, such as tissue biopsy, enlargement procedure, injection of drug. Needle inserting type interventional procedure using the needle inserted into the inside thereof is an example of the interventional procedure. The needle inserting type interventional procedure may be used in most of the interventional procedure, such as tissue biopsy on chest, abdomen and various focus of body, treatment of high frequency, alcohol, refrigeration, radiation and so on, and access for stent insertion or conduit insertion.

For performing the above-mentioned interventional procedure, the needle is inserted into the body with watching the inside of the body using the radiographic imaging device.

Conventionally, in the interventional procedure, the operator manually inserts the needle into the body, and thus the operator is exposed to the harmful circumstances including the radiation generated from the radiographic imaging device such as the X-ray and so on.

Thus, the operator is hard to be prevented from the harmful circumstances, and the needle is inserted only by the experience or skill of the operator and thus the needle is hard to be correctly inserted.

Accordingly, the interventional procedure using a robot with a remote control is necessary, and for performing the above, a process for the interventional procedure should be newly developed. Here, an order from the operator is provided to a slave robot and a needle inserting module, with optimized processes and types, and thus a maser device for the interventional procedure providing an information in the intervention procedure to the operator is also necessary.

Related prior art is Korean laid-open patent application No. 2013-0015437 which is disclosed on Feb. 14, 2013.

SUMMARY

The present invention is developed to solve the above-mentioned problems of the related arts. The present invention provides a handle unit for interventional procedure capable of transmitting a moving order of an operator to a slave robot and a needle driver, providing an haptic feedback on a limit of degrees of freedom on the operation proper to the interventional procedure and an information generated in the interventional procedure to the operator, in the remote control interventional procedure system developed for performing the interventional procedure with a remote control using a robot.

In addition, the present invention also provides a master device for interventional procedure using the handle unit.

In addition, the present invention also provides a remote control interventional procedure system using the master device According to an example embodiment, a handle unit is gripped by an operator corresponding to movement of a needle for the interventional procedure. The handle unit includes a gripper, a mode selection module and a linear motion module. The gripper is gripped by the operator. The mode selection module is equipped to the gripper, and selects one of motion modes including a linear motion mode, a rotational motion mode and a plane motion mode. The needle linearly moves with one degree of freedom in the linear motion mode. The needle rotationally moves with two degrees of freedom in the rotational motion mode. The needle moves in a plane with two degrees of freedom in the plane motion mode. The linear motion module performs the linear motion of the needle based on the selection of the mode selection module, and is equipped to the gripper.

In an example, linear motion module may include an inserting guider, an inserting shaft, a linear motion sensor, a combining block and a returning elastic part. The inserting guider may be combined with an inside of the gripper. A guiding rail may be longitudinally formed in a longitudinal direction. The inserting shaft may be combined with the inserting guider at a side of the guiding rail, with moving back and forth. The linear motion sensor may sense a position of the inserting shaft. The combining block may be slidably combined with the guiding rail with combined with the inserting shaft, and be connected to the linear motion sensor. The returning elastic part may be equipped to the guiding rail, and return the combining block to an initial position.

In an example, the linear motion module may further include a guiding plate combined with the linear motion sensor and the gripper, and supporting the combining block to move.

In an example, the gripper may include a linear body, a control body and a support body. The linear body may have the linear motion module inside thereof, and may be gripped by the operator. The control body may be protruded at a first side of the linear body to form a sectional area larger than that of the linear body, have the mode selection module, and expose a control lever controlling the linear motion module. The support body may be protruded at a second side of the linear body to form a sectional area larger than that of the linear body.

In an example, the handle unit may further include a haptic generating module vibrating the gripper or the linear motion module.

According to another example embodiment, a master device for interventional procedure includes the handle unit mentioned above, a rotational motion module and a plane motion module. The rotational motion module rotates the needle based on the selection of the rotational motion mode, and is combined with the gripper. The plane motion module moves the needle in a plane based on the selection of the plane motion mode, and is combined with the rotational motion module.

In an example, the handle unit may further include a clutch module determining an operation of one of the linear motion module, the rotational motion module and the plane motion module, corresponding to the motion mode selected by the mode selection module.

In an example, the rotational motion module may further include a first rotation base combined with the plane motion module, a second rotation base combined with the first rotation base to be rotated with a first rotational axis, a gripper combiner combined with the gripper, and combined with the second rotation base to be rotated with a second rotational axis crossing the first rotational axis, a first rotation driver equipped to the first rotation base, and providing rotational reaction force to the second rotation base, and a second rotation driver equipped to the second rotation base, and providing rotational reaction force to the gripper combiner.

In an example, the rotational motion module may further include a first absolute angle detector equipped to the first rotational axis, and detecting a rotational state of the second rotation base, and a second absolute angle detector equipped to the second rotational axis, and detecting a rotational state of the gripper combiner. The rotational motion of the needle may be performed based on the detection of the first absolute angle detector and the detection of the second absolute angle detector, the first rotational driver and the second rotational driver may be respectively operated based on the detection of the first absolute angle detector and the detection of the second absolute angle detector, with a start signal starting the motion of the needle or an end signal finishing the motion of the needle, for returning the handle unit to be a neutral position.

In an example, the rotational motion module may further include a weight balancer maintaining a weight balance between the first rotational base and the second rotational base.

In an example, the plane motion module may include a first plane base, a second plane base spaced apart from the first plane base, a first centering block slidably combined with the first plane base along a first plane direction, with combined with the second plane base, and a second centering block slidably combined with the second plane base along a second plane direction crossing the first plane direction, with combined with the rotational motion module.

In an example, the plane motion module may further include a first plane motion detector detecting a moving state of the first centering block with respect to the first plane base, and a second plane motion detector detecting a moving state of the second centering block with respect to the second plane base. The rotational motion of the needle may be performed based on the detection of the first plane motion detector and the detection of the second plane motion detector. The first rotational driver and the second rotational driver may be respectively operated based on the detection of the first plane motion detector and the detection of the second plane motion detector, with a start signal starting the motion of the needle or an end signal finishing the motion of the needle, for returning the handle unit to be a neutral position.

According to still another example embodiment, a remote control interventional procedure system operating a needle with five degrees of freedom includes the master device mentioned above, a needle driver linearly moving the needle based on an operation of the linear motion module, a slave robot rotationally moving the needle based on an operation of the rotational motion module, or moving the needle in a plane based on an operation of the plane motion module, and an interventional control unit controlling the needle driver and the slave robot based on an operation of the master device.

According to the present example embodiments, in the remote control interventional procedure system for performing the interventional procedure using a robot, an order from the operator may be provided to the slave robot and the needle driver, and an haptic feedback on a limit of degrees of freedom on the operation proper to the interventional procedure and an information generated in the interventional procedure may be provided to the operator.

In addition, the operator grasping the gripper may control the linear motion module and the mode selection module at the same time with one hand of the operator, and may control the linear motion of the needle and a rolling motion of the needle easily.

In addition, the operator may easily grasp the gripper. The mode may be easily converted and one of the linear motion, the rolling motion, the rotational motion and the plane motion may be selected to operate the needle, with operating the clutch module by a finger corresponding to the shape of gripping the gripper by the operator.

In addition, the gripper clarifies the linear motion with one degree of freedom, so as to stably provide the linear motion state of the inserting shaft to the needle. Thus, the linear motion of the needle may be accurately controlled based on the linear motion of the inserting shaft.

In addition, the insertion of the needle into the human body may be detected correspond to the linear motion of the inserting shaft. The operator may detect dangerous situation of the interventional procedure when the needle is in a predetermined cautious area.

Thus, the needle may be prevented from damaging the inside of the human body with the predetermined cautious area, and the patient may be properly protected and the medical accident may be prevented in the interventional procedure.

In addition, for each motion of the gripper, the control position of the gripper may be fixed so that the operator may recognize the arrangement and the inserting of the needle in the slave robot.

In addition, the needle may be motioned more correctly, an absolute position of the needle may be detected, and a weight balance of the handle unit may be maintained.

In addition, an interface for the operator may be simplified and easily used, and the handle unit may be in a neutral position based on the start signal and the end signal, so that the operator may control the handle unit more stably.

In addition, the handle unit may include buttons only necessary for the interventional procedure, a dangerous signal may be provided to the operator using a vibrating motor, and mechanism for operating the clutch module is applied to enhance the operation of the clutch.

In addition, for the rotation motion of the needle with two degree of freedom or the plane motion of the needle with two degree of freedom, belt-pulley mechanism and a connection between a driver and a brake are simplified, and friction force and driving force or fixing force may be properly provided to operate the interventional procedure.

In addition, the friction force generated from the master device in the rotational motion of the needle with two degrees of freedom may be controlled or prevented. The slave robot may be smoothly rotated along the first rotational direction with respect to the first rotational axis, the second rotational direction with respect to the second rotational axis, and the mixed rotational direction crossing the first and second rotational directions.

In addition, the haptic feedback may be performed for the plane motion of the needle with two degrees of freedom and the linear motion of the needle with one degrees of freedom, to protect the patient from the needle.

In addition, the reaction force may be provided corresponding to the motion of the needle with each degree of freedom and the needle may be stopped at the predetermined cautious area.

In addition, the needle may be prevented from damaging the human body at the predetermined cautious area, to protect the patient in the interventional procedure and to protect the medical accident.

In addition, the rotational motion module is not operated with the linear motion mode or the plane motion mode, and quantity of motion of the rotational motion module may be accurately detected for the rotational motion of the gripper with two degrees of freedom.

In addition, the linear motion with one degree of freedom, the rotational motion with two degrees of freedom, and the plane motion with two degrees of freedom may be clearly discriminated, the needle may be precisely controlled for each motion, and the position of the needle may be accurately and precisely controlled.

In addition, each motion may be stably provided to the needle driver and the slave robot, and thus negligent accident due to the malfunction of the mode selection may be prevented.

In addition, using the master device for the interventional procedure, the needle may be automatically inserted into the human body, and the operator may be prevented from being exposed to radiation. In addition, as five degrees of freedom of the needle, the linear motion with one degree of freedom, the rotational motion with two degrees of freedom and the plane motion with two degrees of freedom may be selectively performed, so that the needle may be inserted into the human body more accurately, the needle may be prevented to be vibrated due to the operation of the master device in the inserting into the human body, and the selected motion mode may be only performed without intervening the other motion modes, in controlling the master device.

In addition, the motion of the needle may be enlarged, the degree of freedom of the needle may be also enlarged, and the rotation motion with two degrees of freedom and the plane motion with two degrees of freedom may be limited to prevent the vibration of the needle, and thus the needle may be inserted more stably and more accurately.

In addition, the interface for the master device for the interventional procedure may be simplified in using the master device, and the needle inserting type remote control interventional procedure and the processes thereof may be more optimized.

In addition, the driving input and the reaction force may be freely performed for each motion, each motion of the needle may be separated, each motion mode may be clearly discriminated for each separated motion, and further each individual operation may be easily performed at each motion mode.

DETAILED DESCRIPTION

Figure 1:
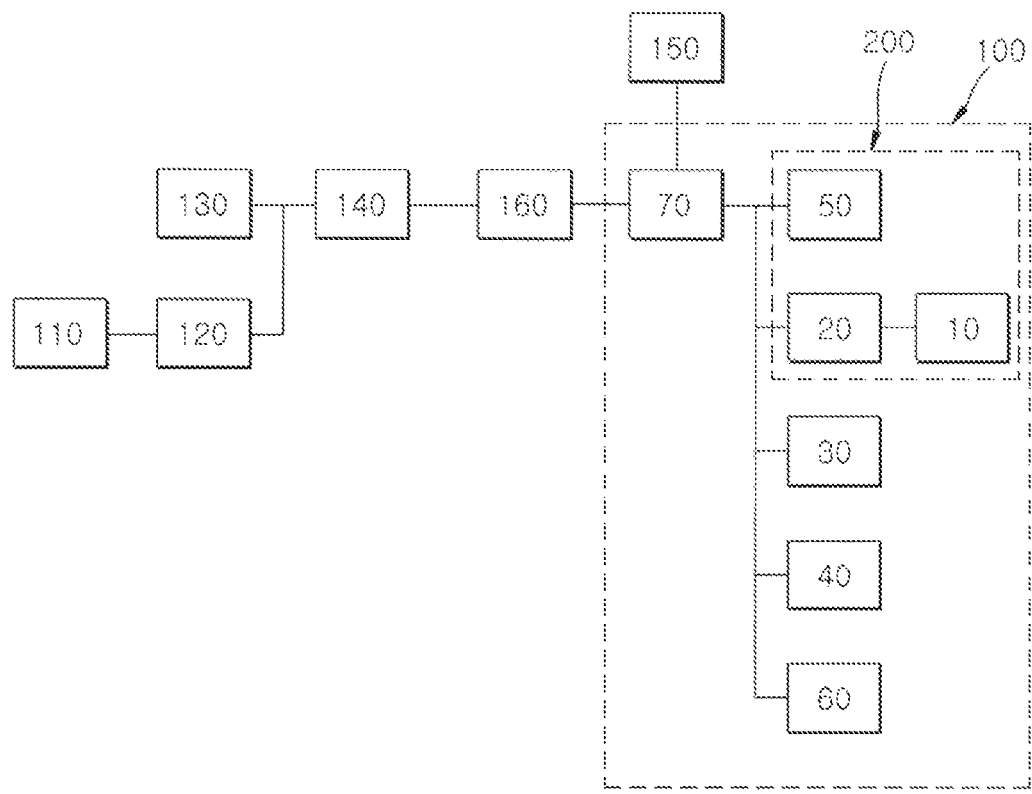
FIG. 1 is a block diagram illustrating a remote control interventional procedure system according to an example embodiment of the present invention.

The invention is described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Same elements or components are expressed with same reference numerals in the drawings.

Figure 2:
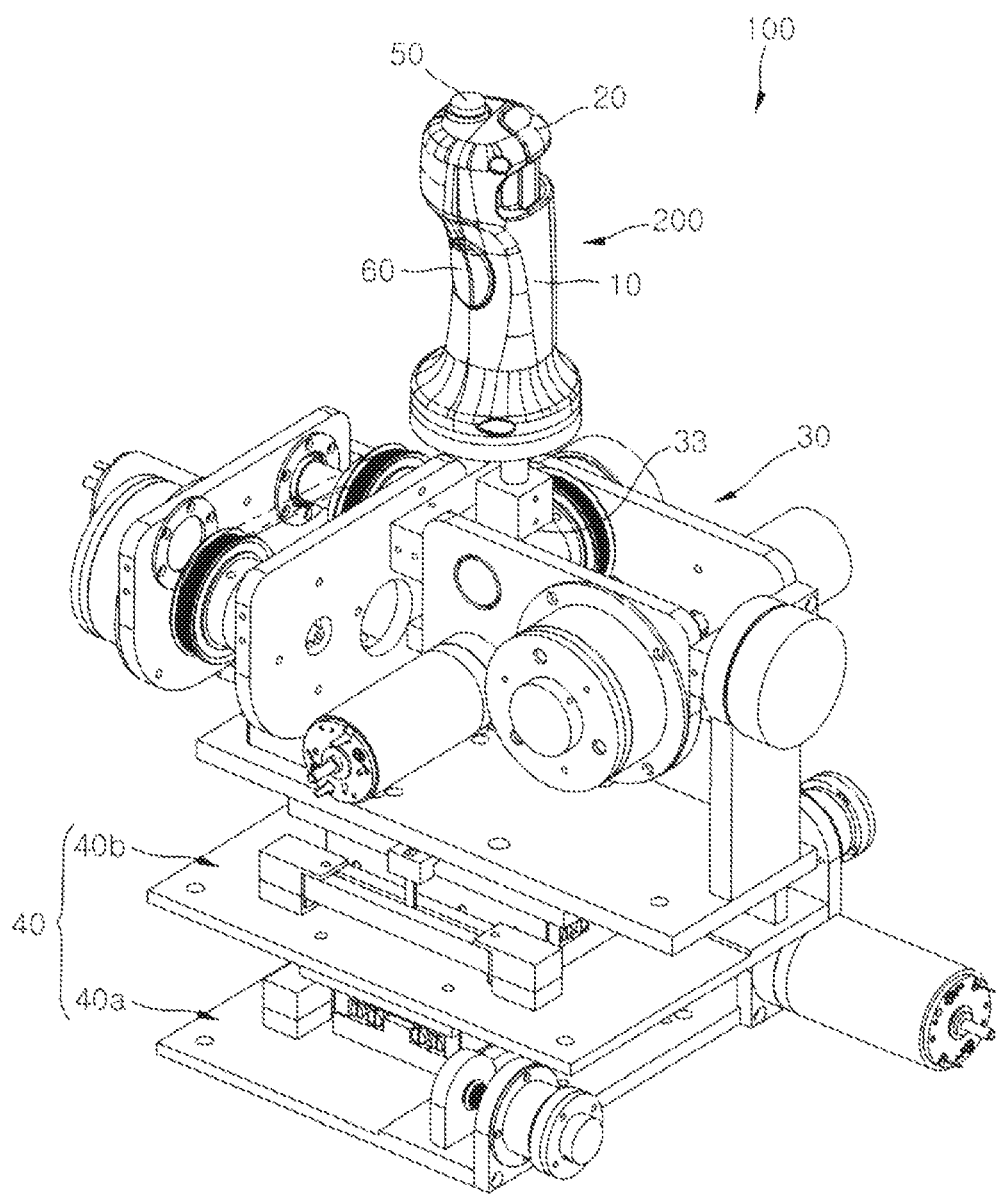
FIG. 2 is a perspective view illustrating a master device for interventional procedure of FIG. 1.
Figure 3:
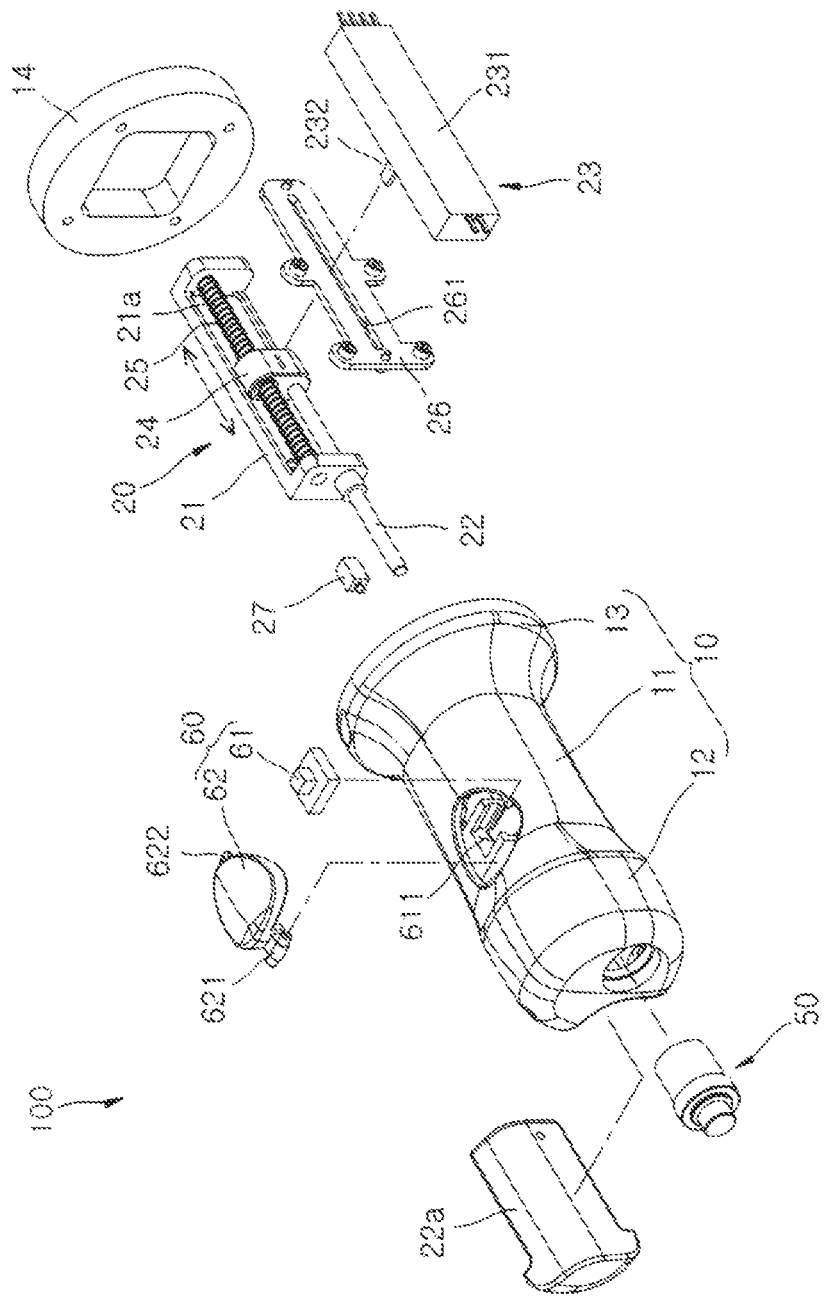
FIG. 3 is an exploded perspective view illustrating a handle unit of FIG. 2.
Figure 4:
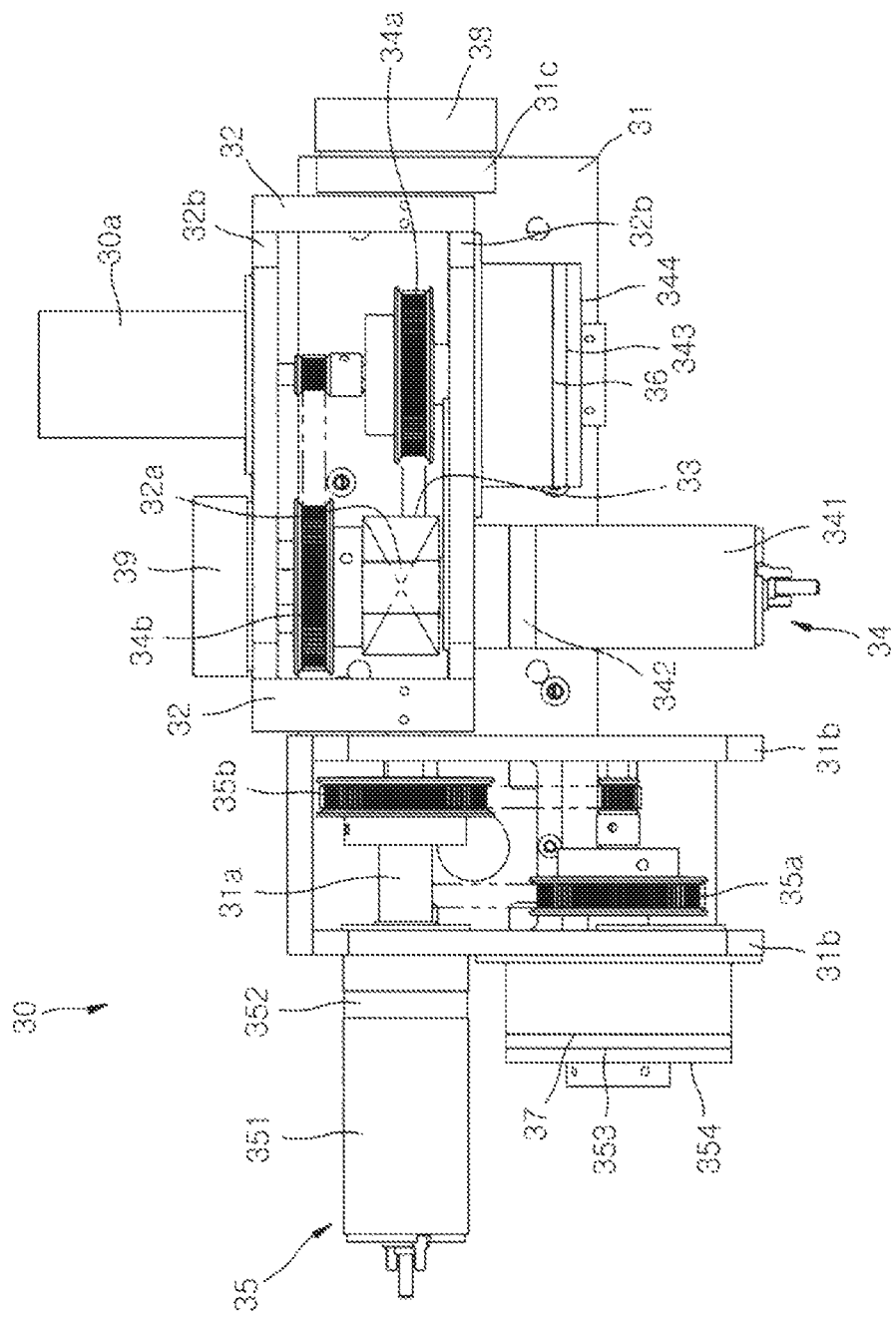
FIG. 4 is a side view illustrating a rotational motion module of FIG. 2.
Figure 5:
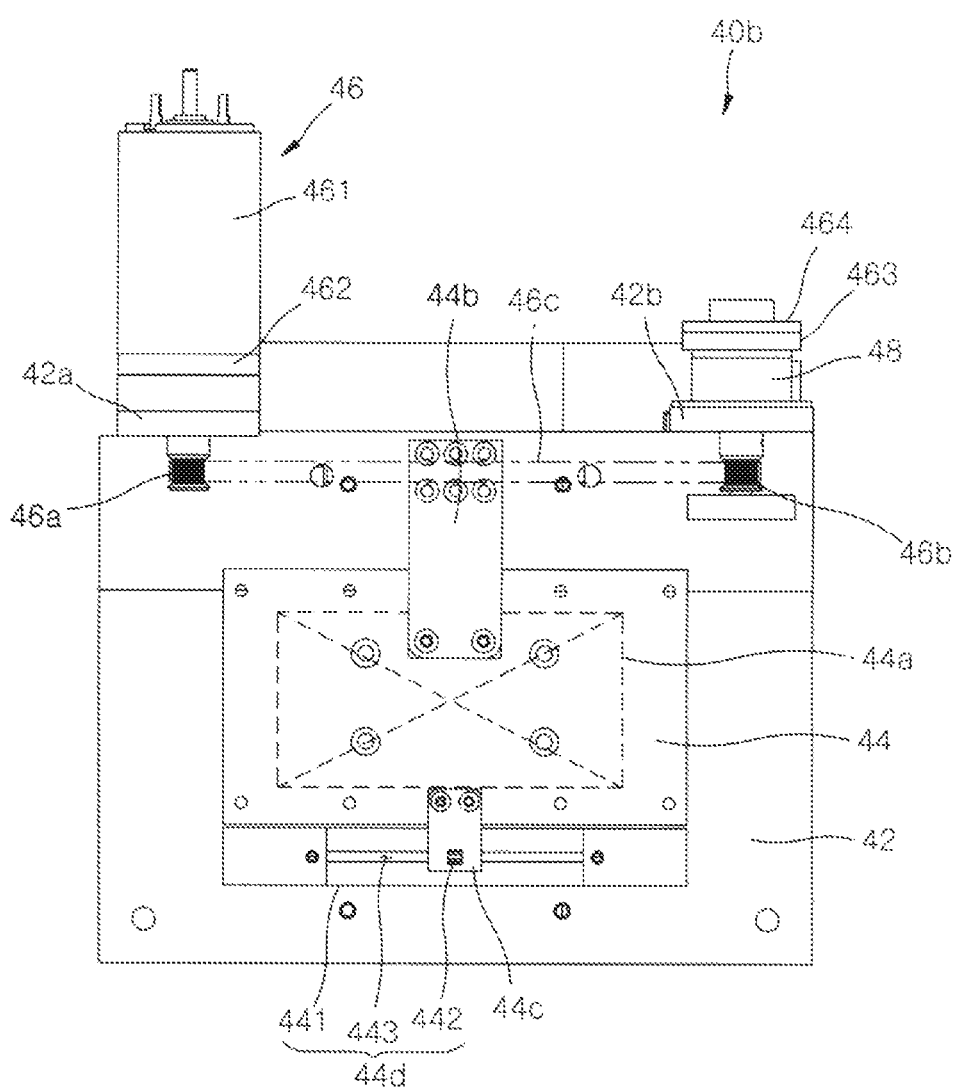
FIG. 5 is a side view illustrating a second plane base and a second centering block of a plane motion module of FIG. 2.
Figure 6:
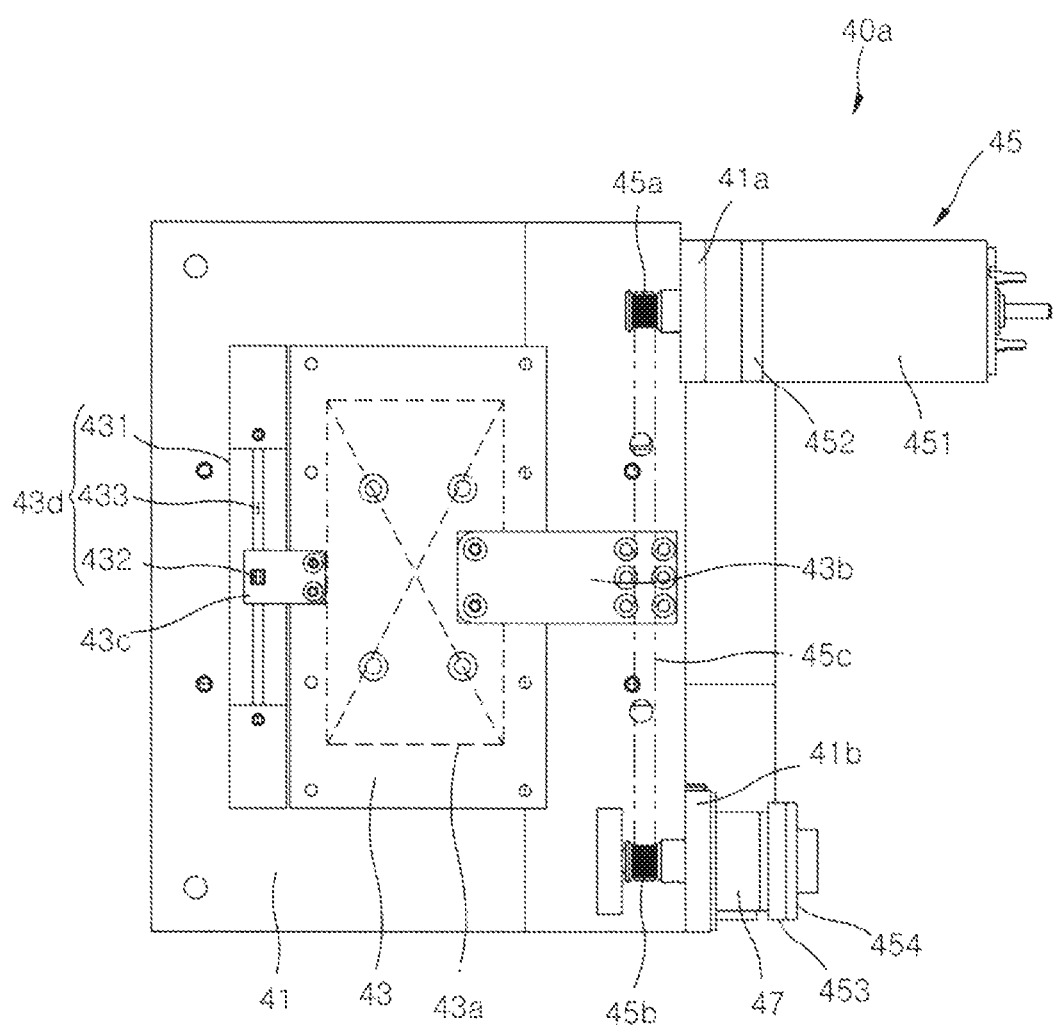
FIG. 6 is a side view illustrating a first plane base and a first centering block of a plane motion module of FIG. 2.
Figure 7:
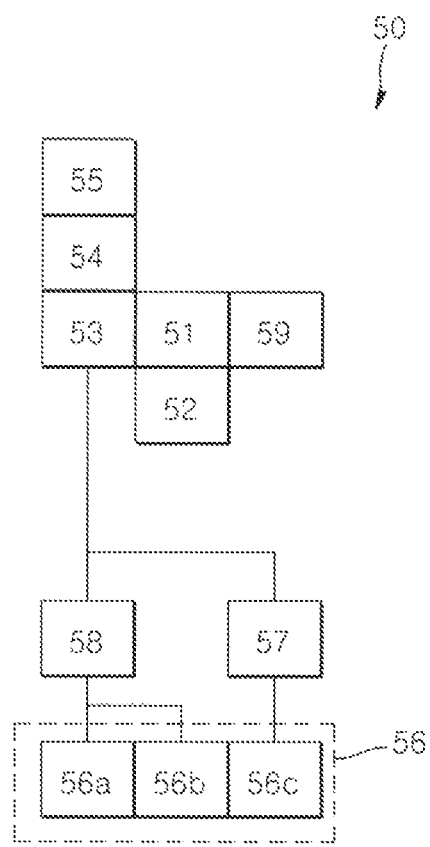
FIG. 7 is a block diagram illustrating a rolling controller and a mode selection module of FIG. 1.

FIG. 1 is a block diagram illustrating a remote control interventional procedure system according to an example embodiment of the present invention. FIG. 2 is a perspective view illustrating a master device for interventional procedure of FIG. 1. FIG. 3 is an exploded perspective view illustrating a handle unit of FIG. 2. FIG. 4 is a side view illustrating a rotational motion module of FIG. 2. FIG. 5 is a side view illustrating a second plane base and a second centering block of a plane motion module of FIG. 2. FIG. 6 is a side view illustrating a first plane base and a first centering block of a plane motion module of FIG. 2. FIG. 7 is a block diagram illustrating a rolling controller and a mode selection module of FIG. 1.

Referring to FIGS. 1 to 7, the remote control interventional procedure system according to the present example embodiment operates the needle 110 in a motion with five degrees of freedom including a rotational motion of two degrees of freedom, a plane motion of two degrees of freedom, and a linear motion of one degree of freedom.

In addition, the remote control interventional procedure system may further operate the needle 110 with a rolling motion.

The system includes a master device 100, a needle driver 120, a slave robot 130 and an interventional control unit 140.

The master device 100 remotely controls the needle driver 120 and the slave robot 130, so as to operate the needle 110 in the motion with five degrees of freedom and the rolling motion. The master device 100 is explained in detail below.

The needle 110 is combined to the needle driver 120, and the needle driver 120 operates the needle 110 in the linear motion with one degree of freedom, or in the rolling motion.

The needle driver 120 is combined to the slave robot 130, and the slave robot 130 operates the needle 110 in the rotational motion with two degrees of freedom, or in the plane motion with two degrees of freedom.

The interventional control unit 140 controls the operation of the needle driver 120 and the slave robot 130, according to the operation of the master device 100. The interventional control unit 140 exchanges information with a master control unit 70 equipped to the master device 100, and updates the information required to the operation control.

Thus, an operator controls the master device 100, so that the needle driver 120 and the slave robot 130 may be remotely controlled, the needle 110 may be accurately positioned at a position for the interventional procedure, the needle 110 may be inserted into a human body, and further the needle 110 may be operated in the rolling motion.

Here, the linear motion with one degree of freedom may be defined as the needle 110 moves linearly along a longitudinal direction with respect to the needle 110. The linear motion with one degree of freedom may be performed as an inserting shaft 22 moves back and forth along an inserting guider 21.

In addition, the rotational motion with two degrees of freedom may be defined as the needle 110 moves with motions of yawing or pitching. The rotational motion with two degrees of freedom may be performed as a gripper 10 rotates along a first rotational direction with respect to a first rotational axis 31a, rotates along a second rotational direction with respect to a second rotational axis 32a and rotates along a complex rotational direction crossing the first and second rotational directions, in a rotational motion module 30.

In addition, the plane motion with two degrees of freedom may be defined as the needle 110 moves along an X axis direction or along a Y axis direction with respect to a virtual plane including the needle 110. The plane motion with two degrees of freedom may be performed as the gripper 10 moves along a first plane direction or along a second plane direction substantially perpendicular to the first plane direction, in a plane motion module 40.

In addition, the rolling motion may be defined as the needle 100 rotates in itself with respect to the needle 100 as an axis. The rolling motion may be performed as a rolling controller 55 rotates.

The reference numeral 150 is a display which displays an interventional procedure and is provided to the operator at a side of master device 100. The reference numeral 160 is a connecting unit connecting a master unit 70 of the master device 100 with the interventional control unit 140 for exchanging information.

Hereinafter, the master device for the interventional procedure is explained.

The master device 100 for the interventional procedure according to the present example embodiment performs the motions of the needle 110 with five degrees of freedom and the rolling motion of the needle 110, and is used for the remote control interventional procedure system. The master device 100 according to the present example embodiment is controlled by the operator to perform the linear motion of the needle 110 with one degree of freedom, the rotational motion of the needle 110 with two degrees of freedom, the linear motion of the needle 110 with two degrees of freedom, and the rolling motion of the needle 110.

The master device 100 accurately positions the needle 110 at an inserting position of the needle 110, with the rotational motion with two degrees of freedom and the plane motion with two degrees of freedom of the gripper 10, and stably inserts the needle 110 into the human body with the linear motion with one degree of freedom using the linear motion module 20. In addition, the needle 110 rolls according as the rolling controller 55 of the mode selection module 50 is rotated.

The master device 100 according to the present example embodiment includes a handle unit 200, a rotational motion module 30 and a plane motion module 40.

The handle unit 200 includes the gripper 10, the mode selection module 50 and a linear motion module 20, and may further include one of a clutch module 60 and a haptic generating module 70. The handle unit 200 may be the handle unit for the interventional procedure of the present example embodiment.

The gripper 10 is configured to be grasped by the operator, and has a column shape with an opening at a center thereof so that the linear motion module 20 and the mode selection module 50 are equipped to the gripper 10. Protrusions are formed on an outer surface of the gripper 10 to prevent the operator from being slipped.

The gripper 10 includes a linear body 11, a control body 12 and a support body 13.

The linear motion module is equipped to an inside of the linear body 11, and the operator grasps the linear body 11. The linear body 11 has a column shape with an opening at a center thereof so that the linear motion module 20 is equipped to the linear body 11.

The control body 12 is protruded from a first side of the linear body 11 to have an area larger than that of the linear body 11. The mode selection module 50 is equipped to the control body 12, and a control lever 22a is exposed to control the linear motion module 20.

The support body 13 is protruded from a second side of the linear body 11 to have an area larger than that of the linear body 11.

In addition, the gripper 10 may further include a connecting body 14 which is combined with the linear body 11 and with which a gripper combiner 33 is combined. The connecting body 14 has a connecting groove for the combination with the gripper combiner 33.

Here, the linear body 11 of the gripper 10 is concaved with a curved or arched shape, so that the operator may control the gripper 10 more conveniently, grasp the gripper 10 more stably, and be prevented from being slipped along a longitudinal direction of the gripper 10 in moving the gripper 10.

The mode selection module 50 is equipped to the gripper 10. The mode selection module 50 selects one motion mode for the needle 110 among the linear motion mode for the linear motion with one degree of freedom, the rotational motion mode for the rotational motion with two degrees of freedom, and the plane motion mode for the plane motion with two degrees of freedom. Then, the mode selection module 50 selects one of the linear motion mode for operating the linear motion module 20, the rotational motion mode for operating the rotational motion module 30, and the plane motion mode for operating the plane motion module 40. In addition, the mode selection module 50 may select the rolling motion mode for the rolling motion of the needle 110. The rolling motion mode is explained to be selected with the linear motion mode at the same time, but may be independently selected without the linear motion mode.

For example, the mode selection module 50 includes a slide block 51, a slide guide 52, a mode selection block 53, a control shaft 54, a rolling controller 55, a mode selector 56, a first converting detector 57 and a second converting detector 58. The slide block 51 is equipped to the gripper 10, to move slidably. The slide guide 52 is combined with the slide block 51, to move slidably. The mode selection block 53 is combined with the slide block 51. The control shaft 54 is combined with the mode selection block 53, with an up and down motion or a rotational motion. The rolling controller 55 is combined and fixed with the control shaft 54. The mode selector 56 determines one motion mode among the rotational motion mode, the plane motion mode and the linear motion mode according to the up and down motion of the control shaft 54 or the sliding motion of the sliding block 51. The first converting detector 57 is connected to the mode selector 56 and transmits a first signal of the up and down motion of the control shaft 54 to the mode selector 56. The second converting detector 58 is connected to the mode selector 56 and transmits a second signal of the sliding motion of the slide block 51 to the mode selector 56. The mode selection module 50 may further include a slide switch 59 selecting the sliding motion of the slide block 51, to switch or convert the motion mode more clearly and easily.

A fixing intercept is concavely formed at the control shaft 54, and a fixing hole is formed through the rolling controller 55 corresponding to the fixing intercept. Then, an additional connecting member is screw-combined with the fixing hole to be pressurized and fixed to the fixing intercept, and thus the rolling controller 55 is fixed to the control shaft 54. When the control shaft 54 has a cylindrical shape, the rotation of the rolling controller 55 is correctly transmitted to the control shaft 54 and the rolling controller 55 is fixed to the control shaft 54.

Although not shown in the figure, the control shaft 54 has a polygonal cross-sectional shape to be inserted into the rolling controller 55, and thus the rolling controller 55 is fixed to the control shaft 54. In addition, an additional connecting member passes through the rolling controller 55 to be screw-combined, and additional connecting member pressurizes, insert-combined or screw-combined with the control shaft 54, and thus the rolling controller 55 is fixed to the control shaft 54.

A method for selecting a motion mode in the mode selection module 50 and a method for performing the rolling motion of the needle 110, are explained.

First, the mode selector 56 discriminates a first selector 56a to which the first converting detector 57 is connected, and a second selector 56b to which the second converting detector 58 is connected.

Then, with the first converting detector 57 and the second converting detector 58 connected to the first selector 56a and the second selector 56b respectively, the mode selector 56 selects one of the plane motion mode, the rotational motion mode and the liner motion mode (or the rolling motion mode), based on the first signal or the second signal. Here, in an initial position, the rotational motion mode is selected. As the control shaft 54 is lifted up, the plane motion mode is selected based on the first signal. As the slide block 51 moves slidably, the linear motion mode or the rolling motion mode is selected based on the second signal.

Then, the mode selection module 50 is predetermined as the rotational motion mode at the initial position. The operator controls the gripper 10 to operate the rotational motion module 30. Here, the operator controls the gripper 10 with operating the clutch module 60, to operate the rotational motion module 30.

When the operation of the rotational motion module 30 is finished, the operation of the clutch module 60 is released, and the operation of the rotational motion module 30 is stopped using a first rotational brake 36 and a second rotational brake 37 in the rotational motion module 30 to maintain the gripper 10 in an inclined position.

In addition, when the operation of the rotational motion module 30 is finished, the control shaft 54 is lifted up to transmit the first signal to the mode selector 56, and thus the plane motion mode is selected. Thus, the operator controls the gripper 10 to operate the plane motion module 40 only. Here, the operator controls the gripper 10 with operating the clutch module 60, to operate the plane motion module 40 only.

After the operation of the plane motion module 40 is finished, the operation of the clutch module 60 is released, and the operation of the plane motion module 40 is stopped using a first plane brake 46 and a second plane brake 48 in the plane motion module 40 to maintain the gripper 10 in a plane moved position.

In addition, when the operation of the plane motion module 40 is finished, the control shaft 54 is slidably moved to transmit the second signal to the mode selector 56, and thus the linear motion mode or the rolling motion mode is selected. Here, the slide switch 59 is turned on, and thus the second signal is transmitted to the mode selector 56. Thus, the operator controls the needle to move with the linear motion with one degree of freedom according to the movement of the inserting shaft 22. In addition, the operator rotates the rolling controller 55 to perform the rolling motion of the needle 110. Here, the operator controls the needle 110 to move with the linear motion with one degree of freedom or the rolling motion, with operating the clutch module 60.

In addition, the linear motion module 20 forces to stop operating the rotational motion module 30 and the plane motion module 40, and is to be operated, according to the movement of the inserting shaft 220, when any one of the above-mentioned three motion modes is selected.

Alternatively, the mode selection module 50 includes a slide block 51, a slide guide 52, a mode selection block 53, a control shaft 54, a rolling controller 55, a mode selector 56, a first converting detector 57 and a second converting detector 58. The slide block 51 is equipped to the gripper 10, to move slidably. The slide guide 52 is combined with the slide block 51, to move slidably. The mode selection block 53 is combined with the slide block 51, with an up and down motion. The control shaft 54 is combined with the mode selection block 53, with a rotational motion. The rolling controller 55 is combined and fixed with the control shaft 54. The first converting detector 57 determines one motion mode among the rotational motion mode, the plane motion mode and the linear motion mode according to the up and down motion of the mode selection block 53. The second converting detector 58 selects one of two motion mode not selected by the first converting detector 57 among the above-mentioned three motion mode, according to the sliding motion of the slide block 51, the mode selector 56 is connected to one of the first converting detector 57 and the second converting detector 58 according to the up and down motion of the mode selection block 53 or the sliding motion of the slide block 51, and determines one of the rotational motion mode, the plane motion mode and the linear motion mode.

Here, when the first converting detector 57 determines the motion mode among three motion modes according to the sliding motion of the slide block 51, the second converting detector 58 selects the motion mode in the remained two motion modes not selected by the first converting detector 57 according to the up and down motion of the mode selection block 53. Thus, an 'L' shape path is formed according to the up and down motion of the mode selection block 53 and the sliding motion of the slide block 51, and then one motion mode among three motion modes is selected by the first converting detector 57 or the second converting detector 58 connected to three apexes.

A method for selecting the motion mode in the mode selection module 50, and a method for performing the rolling motion of the needle 110 are explained.

First, the mode selector 56 discriminates a first selector 56a to which the first converting detector 57 is connected according to the up and down motion of the mode selection block 53, a second selector 56b to a first side of which the second converting detector 58 is connected according to the sliding motion of the slide block 51, and a third selector 56c to a second side of which the second converting detector 58 is connected according to the slide motion of the slide block 51.

Then, one of the plane motion mode, the rotational motion mode and the linear motion mode is determined according to the connection of one of the first selector 56a, the second selector 56b and the third selector 56c. Here, when the first converting detector 57 is connected to the first selector 56a, the plane motion mode is selected. When the second converting detector 58 is connected to the second selector 56b, the rotational motion mode is selected. When the second converting detector 58 is connected to the third selector 56c, the linear motion mode or the rolling motion mode is selected.

In addition, the mode selector 56 discriminates a first selector 56a to which the first converting detector 57 is connected according to the sliding motion of the slide block 51, a second selector 56b to a first side of which the second converting detector 58 is connected according to the up and down motion of the mode selection block 53, and a third selector 56c to a second side of which the second converting detector 58 is connected according to the up and down motion of the mode selection block 53.

Then, the second converting detector 58 of the mode selection module 50 is connected to the second selector 56b at the initial position and is to be selected as the rotational motion mode. The operator controls the gripper 10 to operate the rotational motion module 30 only. Here, the operator controls the gripper 10 to operate the rotational motion module 30, with operating the clutch module 60.

When the operation of the rotational motion module 30 is finished, the operation of the clutch module 60 is released, and the operation of the rotational motion module 30 is stopped using a first rotational brake 36 and a second rotational brake 37 in the rotational motion module 30 to maintain the gripper 10 in an inclined position.

In addition, when the operation of the rotational motion module 30 is finished, the control shaft 54 is lifted up and down to disconnect the second converting detector 58 with the second selector 56b and the third selector 56c, and to connect the first converting detector 57 with the first selector 56a. Then, the plane motion mode is selected. Thus, the operator controls the needle to operate the plane motion module 40 only. Here, the operator controls the gripper 10 to operate the plane motion module 40, with operating the clutch module 60.

When the operation of the plane motion module 40 is finished, the operation of the clutch module 60 is released, and the operation of the plane motion module 40 is stopped using a first plane brake 47 and a second plane brake 48 in the plane motion module 40 to maintain the gripper 10 in a plane moved position.

In addition, when the operation of the plane motion module 40 is finished, returned into the initial position, and the control shaft 54 is slidably moved to release the connection between the first converting detector 57 and the first selector 56a and the connection between the second converting detector 58 and the second selector 56b, and to connect the second converting detector 58 with the third selector 56c. Then, the linear motion mode or the rolling motion mode is selected. Thus, the operator controls the needle to move in the linear motion with one degree of freedom according to the movement of the inserting shaft 22. In addition, the operator rotates the rolling controller 55 to operate the needle with the rolling motion. Here, the operator rotates the rolling controller 55 to operate the needle, with operating the clutch module 60.

In addition, the linear motion module 20 forces to stop operating the rotational motion module 30 and the plane motion module 40, and is to be operated, according to the movement of the inserting shaft 220, when any one of the above-mentioned three motion modes is selected.

The linear motion module 20 is equipped to the gripper 10. The linear motion module 20 performs the linear motion of the needle 110 with one degree of freedom, according to the selection of the linear motion mode.

The linear motion module 20 includes an inserting guider 21, an inserting shaft 22, a linear motion sensor 23, a combining block 24 and a returning elastic part 25, and may further include a guiding plate 26.

The inserting guider 21 is combined with an inside of the gripper 10. The guiding rail 21a is formed in the inserting guider 21 along a longitudinal direction. The inserting guider 21 has a 'U' shape, and the guiding rail 21a is longitudinally formed along the inserting guider 21.

The inserting shaft 22 is combined with the inserting guider 21 and move back and forth in the inserting guider 21 at a first side of the guiding rail 21a. A first side of the inserting shaft 22 is protruded from the inserting guider 21. A control lever 22a is combined with a first side of the inserting shaft 22, and thus the operator moves the inserting shaft 22 back and forth with a finger very easily. The control lever 22a is exposed from the control body 12 of the gripper 10, and is supported by the control body 12 to be slidably moved, so that the inserting shaft 22 may be prevented from being freely moved, and the movement of the inserting shaft 22 may be stably.

The linear motion sensor 23 detects the position of the inserting shaft 22, and detects an amount of the linear movement of the inserting shaft 22. The linear motion sensor 23 includes a linear motion selector 231 detecting an initial position, a forward direction movement and a reverse direction movement of the inserting shaft 22, and a linear selection protrusion 232 protrude from the linear motion selector 231 and moving with the inserting shaft 22.

The combining block 24 is combined with the guiding rail 21a and is slidably moves along the guiding rail 21a. The combining block 24 is connected to the linear motion sensor 23 or the linear selection protrusion 232.

Then, the combining block 24 slidably moves along the guiding rail 21a according to the movement of the inserting shaft 22, and moves the linear selection protrusion 232 so that the linear motion selector 231 detects the amount of the linear motion of the inserting shaft 22.

The returning elastic part 25 is equipped to the guiding rail 21a The returning elastic part 25 returns the combining block 24 to the initial position. The returning elastic part 25 includes a coil spring coiled in the guiding rail 21a. Here, the returning elastic part 25 is elastically deformed due to the movement of the inserting shaft 22 or the combining block 24, and when the outer force is released, the returning elastic part 25 returns the combining block 24 back to the initial position due to the elastic restoring force. The returning elastic part 25 elastically supports both sides of the combining block 24.

The guiding plate 26 is combined with the linear motion detector 23, is combined with the gripper 10, and support the combining block 24 to be moved. A guiding slit 261 is formed through the guiding plater 26, along the longitudinal direction of the inserting guider 21. The linear selection protrusion 232 is inserted into the guiding slit 261 to be moved, to prevent the combining block 24 from being freely moved and to stabilize the sliding movement of the combining block 24.

The clutch module 60 is equipped to the gripper 10. Alternatively, not shown in the figure, the clutch module 60 may be equipped to the control body 12.

The clutch module 60 determines an operation of one of the linear motion module 20, the rotational motion module 30 and the plane motion module 30, corresponding to the motion mode selected by the mode selection module 50. In other words, the clutch module 60 may select or release the motion mode corresponding to the operation of the mode selection module 50. Further, the clutch module 60 may select or release an entire operation of the linear motion module 20, the rotational motion module 30 and the plane motion module 40, and the rolling motion of the needle 110.

The clutch module 60 includes a clutch switch 61 determining On/Off based on a clutch motion, and a clutch button 62 operating the clutch switch 61. The clutch switch 61 is combined with a switch mount 611 inside of the gripper 10, and is combined with the gripper 10 to be rotated, with exposed from the griper 10. A pivot axis 621 is included in the clutch button 62 and thus the clutch button 62 is combined with the gripper 10 to be rotated using the pivot axis 621 as an intervening member. In addition, a button position fixer 622 is protruded from the clutch button 62, to limit the rotation of the cutch button 62 and for the clutch button 62 to be stably supported by the gripper 10.

When the clutch module 60 is turned on, the entire motions of the linear motion module 20, the rotational motion module 30 and the plane motion module 40 are operated or the rolling motion of the needle 110 are operated. In addition, when the clutch button is turned off, the needle is not moved even though the entire motions are operated or the rolling motion is operated.

For example, the clutch module 60 is turned on (the clutch module 60 is operated) and the motion mode is selected by the mode selection module 50, and then the motion module corresponding to the selected motion mode is operated to move the needle 110. In addition, the needle is not moved in the remaining motion mode except for the selected motion mode.

In addition, when the clutch module 60 is turned off (the clutch module 60 is not operated), one of the linear motion module 20, the rotational motion mode 30 and the plane motion module 40 may be operated or the rolling controller 55 may be rotated, but the needle 110 is not operated.

Further, when the clutch module 60 is turned off and one of the rotational motion mode or the rolling motion mode is selected, the inserting shaft 22 moves back and forth or the rolling controller 5 is rotated, but the rotational motion module 30 and the plane motion module 40 are fixed and the needle 110 is also maintained to be fixed.

The haptic generating module 70 vibrates the gripper 10 or the linear motion module 20. The haptic generating module 70 vibrates the gripper 10 to provide the operator with a haptic sensing. The haptic generating module 70 vibrates the inserting guider 21 or the inserting shaft 22, to provide the operator with the haptic sensing. The haptic generating module 70 includes a vibrating motor inside of the gripper 10.

When the needle 110 is inserted into a predetermined cautious area, the haptic generating module 70 provides the operator with a state of a linear motion of the inserting shaft 22 in the predetermined cautious area.

Here, a master control unit 70 determines whether the needle 110 is inserted into the predetermined cautious area or not. When the needle 110 is in the predetermined cautious area, the haptic generating module 70 is operated due to the signal from the master control unit and thus the operator feels the vibrations in the gripper 10 or the inserting shaft 22. Here, the inserting shaft 22 moves forwardly and thus the needle 110 moves forwardly. Thus, the haptic generating module 70 warns the operator and the operator recognizes the warning situation in the interventional procedure.

In addition, the master control unit 70 determines whether the needle 110 is inserted into a dangerous area of the predetermined cautious area in which a danger exists. When the needle 110 is inserted into the dangerous area, a stopping signal from the master control unit 70 is transmitted to the needle 110, to stop the needle 110 regardless of the advance of the inserting shaft 22. Then, the needle 110 is not moved even though the operator advances the inserting shaft 22 forwardly.

In addition, when the inserting shaft 22 moves backwardly, the needle 110 also moves backwardly. Here, when the inserting shaft 22 is moved backwardly, the returning signal from the master control unit 70 is transmitted to the needle 110, and thus the needle 110 moves backwardly and gets out of the predetermined dangerous area or the predetermined cautious area.

When the inserting shaft 22 moves backwardly, the master control unit 70 provides the signal concerning the backward movement to the needle 110 to move the needle 110 backwardly.

The rotational motion module 30 is combined with the gripper 10. The rotational motion module 30 performs the rotational motion of the needle 110 with two degrees of freedom as the gripper 10 moves based on the selection of the rotational motion mode.

The rotational motion module 30 includes a first rotation base 31, a second rotation base 32 and a gripper combiner 33. The first rotation base 31 is combined with the plane motion module 40. The second rotation base 32 is combined with the first rotation base 31 and is rotated with respect to a first rotational axis 31a. The gripper 10 is combined with the gripper combiner 33. The gripper combiner 33 is combined with the second rotation base 32, and is rotated with respect to a second rotational axis 32a crossing the first rotational axis 31a. Here, the first and second rotational axes 31a and 32a may be substantially perpendicular to each other.

The rotational motion module 30 may further include a first rotation driver 35 and a second rotation driver 34. The first rotation driver 35 is equipped to the first rotation base 31 and provides a rotational reaction force to the second rotation base 32. The second rotation driver 34 is equipped to the second rotation base 32 and provides the rotational reaction force to the gripper combiner 33. The first and second rotation drivers 35 and 34 may provide the rotational reaction force in the predetermined cautious area or in a correct area.

Here, the first rotation driver 35 includes a first rotation motor 351 and a first encoder 352. The first rotation motor 351 generates the rotational force for the rotational reaction force. The first encoder 352 detects the rotational force of the first rotational motor 351 to control the operation of the first rotation motor 351.

In addition, the second rotation driver 34 includes a second rotation motor 341 and a second encoder 342. The second rotation motor 341 generates the rotational force for the rotational reaction force. The second encoder 342 detects the rotational force of the second rotational motor 341 to control the operation of the second rotation motor 341.

Thus, the first and second rotation drivers 35 and 35 provide the rotational reaction force to the operator, stably.

The rotational motion module 30 may further include a first rotation brake 37 and a second rotation brake 36. The first rotation brake 37 is equipped to the first rotation base 31 and maintains the rotational state of the second rotation base 32. The second rotation brake 36 is equipped to the second rotation base 32 and maintains the rotational state of the gripper combiner 33.

Here, the first rotation brake 37 includes a first harmonic drive 353 controlling a reduction gear ratio of the first rotation motor 351, and a first torque sensor 354 detecting a torque of the first rotation motor 351.

In addition, the second rotation brake 36 includes a second harmonic drive 343 controlling a reduction gear ratio of the second rotation motor 341, and a second torque sensor 344 detecting a torque of the second rotation motor 341.

The first rotation brake 37 and the second rotation brake 36 maintain the rotational state in the predetermined cautious area or in the correct area.

Here, the first rotation driver 35 and the first rotation brake 37 are combined with the first rotation base 31 by means of a first bracket 31b equipped to the first rotation base 31. Here, the first rotation driver 35 is connected to the first rotation brake 37 by means of a first rotation transmitter 35a, and the first rotation brake 37 is connected to the first rotational axis 31a by means of a first stop transmitter 35b. Each of the first rotation transmitter 35a and the first stop transmitter 35b may be a belt combination or a pulley combination.

In addition, the second rotation base 32 is rotationally combined with the first rotation base 31 by means of a first bracket 31b and a sub bracket 31c equipped to the first rotation base 31.

In addition, the second rotation driver 34 and the second rotation brake 36 are combined with the second rotation base 32, by means of a second bracket 32b equipped to the second rotation base 32. Here, the second rotation driver 34 is connected to the second rotation brake 36 by means of a second rotation transmitter 34a, and the second rotation brake 36 is connected to the second rotational axis 32a by means of a second stop transmitter 34b. Each of the second rotation transmitter 34a and the second stop transmitter 34b may be a belt combination or a pulley combination.

In addition, the rotational motion module 30 includes a first absolute angle detector 38 and a second absolute angle detector 39. The first absolute angle detector 38 is equipped to the first rotational axis 31a of the first rotation base 31 and detects the rotational state of the second rotation base 32. The second absolute angle detector 39 is equipped to the second rotational axis 32a of the second rotation base 32 and detects the rotational state of the gripper combiner 33. The first absolute angle detector 38 is equipped to the first rotational axis 31a and the second absolute angle detector 39 is equipped to the second rotational axis 32a.

The first absolute angle detector 38 detects an absolute rotation angle of the second rotational base 32, and the second absolute angle detector 39 detects an absolute rotation angle of the gripper combiner 32. Thus, the rotation angle for the rotational motion with two degrees of freedom may be accurately selected or detected.

Then, the rotational motion of the needle 110 with two degrees of freedom may be performed, based on the detection by the first and second absolute angle detectors 38 and 39.

In addition, the first and second rotation drivers 35 and 34 are respectively operated corresponding to the detection from the first and second absolute angle detectors 38 and 39, to return the handle unit 200 to a neutral position, based on an start signal starting the movement of the needle 10 or an end signal finishing the movement of the needle 110.

Here, the neutral position of the handle unit 200 means that each of the detection from the first and second absolute angle detectors 38 and 39 is zero, and thus the first and second rotation drivers 35 and 34 are operated to meet the absolute rotation angle as zero. In addition, the neutral position of the handle unit 200 means the absolute rotation angle corresponding to the start signal, and thus the first and second rotation drivers 35 and 34 are operated to rotate the needle with the absolute angle, based on the start signal.

In addition, the rotational motion module 30 may further include a weight balancer 30a maintaining a weight between the first rotation base 31 and the second rotation base 32 with respect to the plane motion module 40. The weight balancer 30a is equipped to the second rotation base 32. For example, the weight balance 30a may be disposed along an axis same as one of the second rotational axis 32a, the rotational axis of the second rotation driver 34, and the rotational axis of the second rotation brake 36.

The plane motion module 40 is combined with the rotational motion module 30, and performs the plane motion of the needle 110 with two degrees of freedom by moving the gripper 10 as the selection of the plane motion mode.

The plane motion module 40 is divided into a first plane module 40a and a second plane module 40b. The first plane module 40a moves the needle 110 along a first plane direction with respect to a bottom as the gripper 10 moves. The second plane module 40b moves the needle 110 along a second plane direction with respect to the first plane module 40a as the gripper 10 moves. Here, the first and second plane directions may be cross or perpendicular to each other.

The plane motion module 40 includes a first plane base 41, a second plane base 42, a first centering block 43 and a second centering block 44.

The first plane base 41 is supported by the bottom. The first plane base 41 has a plate shape. The first plane base 41 includes a first motor bracket 41a supporting a first plane driver 45, and a first support bracket 41b supporting a first plane brake 47.

The second plane base 42 is spaced apart from the first plane base 41. The second plane base 42 has a plate shape. The second plane base 42 includes a second motor bracket 42a supporting a second plane driver 46, and a second support bracket 42b supporting a second plane brake 48.

The first centering block 43 is slidably combined with the first plane base 41, with combined with the second plane base 42. The first centering block 43 is slidably combined with the first plane base 41 by means of a first slider 43a. The first slider 43a includes an LM slide block. The first centering block 43 slidably moves along the first plane direction with respect to the first plane base 41. A first fixing bracket 43b connected to a first belt 45c is equipped to the first centering block 43. In addition, a first connecting bracket 43c connected to a first plane motion detector 43d is equipped to the first centering block 43.

The second centering block 44 is slidably combined with the second plane base 42, with combined with the rotational motion module 30. The second centering block 44 is slidably combined with the second plane base 42 by means of a second slider 44a. The second slider 44a includes an LM slide block. The second centering block 44 slidably moves along the second plane direction crossing the first plane direction with respect to the second plane base 42. Here, the first and second plane directions may be perpendicular to each other. A second fixing bracket 44b connected to a second belt 46c is equipped to the second centering block 44. In addition, a second connecting bracket 44c connected to a second plane motion detector 44d is equipped to the second centering block 44.

The plane motion module 40 includes a first plane driver 45 and a second plane driver 46. The first plane driver 45 is connected to the first centering block 43 with combined with the first plane base 41 and provides a reaction force to the sliding movement of the first centering block 43. The second plane driver 46 is connected to the second centering block 44 with combined with the second plane base 42 and provides a reaction force to the sliding movement of the second centering block 44.

The first plane driver 45 is combined with the first plane base 41 by the first motor bracket 41a, and the second plane driver 46 is combined with the second plane base 42 by the second motor bracket 42a. The first and second plane drivers 45 and 46 may provide the reaction force in the predetermined cautious area or in the correct area.

Here, the first plane driver 45 includes a first plane motor 451 generating a rotational force for the rotational reaction force, and a first plane encoder 452 detecting the rotational force of the first plan motor 451 to control the first plane encoder 451.

In addition, the second plane driver 46 includes a second plane motor 461 generating a rotational force for the rotational reaction force, and a second plane encoder 462 detecting the rotational force of the second plane motor 461 to control the second plane encoder 461.

The plane motion module 40 may further include a first plane brake 47 and a second plane brake 48. The first plane brake 47 is connected to the first centering block 43 with combined with the first plane base 41, and maintains the sliding state of the first centering block 43. The second plane brake 48 is connected to the second centering block 44 with combined with the second plane base 42, and maintains the sliding state of the second centering block 44.

The first plane brake 47 is combined with the first plane base 41 by the first support bracket 41b in the first plane driver 45. The second plane base 42 is combined with the second plane base 42 by the second support bracket 42b in the second plane driver 46.

The first and second plane brakes 47 and 48 may maintain the moving state in the predetermined cautious area or in the correct area.

Here, the first plane brake 47 includes a first plane harmonic drive 453 controlling a reduction gear ratio of the first plane motor 451, and a first plane torque sensor 454 detecting a torque of the first plane motor 451.

In addition, the second plane brake 48 includes a second plane harmonic drive 463 controlling a reduction gear ratio of the second plane motor 461, and a second plane torque sensor 464 detecting a torque of the second plane motor 461.

Here, the first plane driver 45 and the first plane brake 47 are connected to each other, by a first driving pulley 45a combined with the rotational axis of the first plane driver 45, a first brake pulley 45b combined with the rotational axis of the first plane brake 47, and a first belt 45c connecting the first driving pulley 45a with the first brake pulley 45b. The first belt 45c is combined with the first fixing bracket 43b. Thus, the first plane driver 45, the first plane brake 47 and the first centering block 43 are connected and operated with each other. Although not shown in the figure, the first plane driver 45 and the first plane brake 47 may be combined with each other using a chain or a sprocket.

In addition, the second plane driver 46 and the second plane brake 48 are connected to each other, by a second driving pulley 46a combined with the rotational axis of the second plane driver 46, a second brake pulley 46b combined with the rotational axis of the second plane brake 48, and a second belt 46c connecting the second driving pulley 46a with the second brake pulley 46b. The second belt 46c is combined with the second fixing bracket 44b. Thus, the second plane driver 46, the second plane brake 48 and the second centering block 44 are connected and operated with each other. Although not shown in the figure, the second plane driver 46 and the second plane brake 48 may be combined with each other using a chain or a sprocket.

In addition, the plane motion module 40 may further include a first plane motion detector 43d detecting a movement of the first centering block 43 with respect to the first plane base 41, and a second plane motion detector 44d detecting a movement of the second centering block 44 with respect to the second plane base 42.

The first plane motion detector 43d includes a first plane motion selector 431 and a first selection protrusion 432. The first plane motion selector 431 detects an initial position, an amount of forward movement and an amount of backward movement of the first centering block 43. The first selection protrusion 432 is protruded from the first plane motion selector 431 and moves together with the first centering block 43. A first plane guider 433 guiding the first selection protrusion 432 is formed in the first plane motion selector 431, to clarify the movement of the first selection protrusion 432. The first selection protrusion 432 is combined with the first connecting bracket 43c, to make the connection with the first centering block 43 much easier.

The second plane motion detector 44d includes a second plane motion selector 441 and a second selection protrusion 442. The second plane motion selector 441 detects an initial position, an amount of forward movement and an amount of backward movement of the second centering block 44. The second selection protrusion 442 is protruded from the second plane motion selector 441 and moves together with the second centering block 44. A second plane guider 443 guiding the second selection protrusion 442 is formed in the second plane motion selector 441, to clarify the movement of the second selection protrusion 442. The second selection protrusion 442 is combined with the second connecting bracket 44c, to make the connection with the second centering block 44 much easier.

The first plane motion detector 43d detects an absolute position of the first centering block 43, and the second plane motion detector 44d detects an absolute position of the second centering block 44, so that the position for the plane motion with two degrees of freedom may be more clarified.

Then, the needle 110 may be operated in the plane motion with two degrees of freedom, based on the detection of the first and second plane motion detectors 43d and 44d.

In addition, the first and second plane drivers 45 and 46 may be operated corresponding to the detection of the first and second plane motion detectors 43d and 44d, based on the start signal starting the motion of the needle 110 and the end signal finishing the motion of the needle 110, for returning the handle unit 200 to the neutral position.

Here, the neutral position of the handle unit 200 means that each of the detection from the first and second plane motion detectors 43d and 44d is zero, and thus the first and second plane drivers 45 and 46 are operated to meet the absolute position as zero. In addition, the neutral position of the handle unit 200 means the absolute position corresponding to the start signal, and thus the first and second plane drivers 45 and 46 are operated to move the needle with the absolute position, based on the start signal.

The master device for the interventional procedure according to the present example embodiment may further include a master control unit 70. The master control unit 70 controls the operation of the linear motion module 20, the rotational motion module 30 and the plane motion module 40, in relation with the mode selection module 50. The master control unit 70 may replace the information for the motion control, with exchanging the information with the interventional control unit 140.

According to the present example embodiments, in the remote control interventional procedure system for performing the interventional procedure using a robot, an order from the operator may be provided to the slave robot 130 and the needle driver 120, and an haptic feedback on a limit of degrees of freedom on the operation proper to the interventional procedure and an information generated in the interventional procedure may be provided to the operator.

In addition, the operator grasping the gripper 10 may control the linear motion module 20 and the mode selection module 50 at the same time with one hand of the operator, and may control the linear motion of the needle 110 and a rolling motion of the needle 110 easily.

In addition, the operator may easily grasp the gripper 10. The mode may be easily converted and one of the linear motion, the rolling motion, the rotational motion and the plane motion may be selected to operate the needle 110, with operating the clutch module 60 by a finger corresponding to the shape of gripping the gripper 10 by the operator.

In addition, the gripper 10 clarifies the linear motion with one degree of freedom, so as to stably provide the linear motion state of the inserting shaft 22 to the needle. Thus, the linear motion of the needle 110 may be accurately controlled based on the linear motion of the inserting shaft 22.

In addition, the insertion of the needle 110 into the human body may be detected correspond to the linear motion of the inserting shaft 22. The operator may detect dangerous situation of the interventional procedure when the needle 110 is in a predetermined cautious area. Thus, the needle 110 may be prevented from damaging the inside of the human body with the predetermined cautious area, and the patient may be properly protected and the medical accident may be prevented in the interventional procedure.

In addition, for each motion of the gripper 10, the control position of the gripper 10 may be fixed so that the operator may recognize the arrangement and the inserting of the needle 110 in the slave robot 130.

In addition, the needle 110 may be motioned more correctly, an absolute position of the needle may be detected, and a weight balance of the handle unit 200 may be maintained.

In addition, an interface for the operator may be simplified and easily used, and the handle unit 200 may be in a neutral position based on the start signal and the end signal, so that the operator may control the handle unit 200 more stably.

In addition, the handle unit 200 may include buttons only necessary for the interventional procedure, a dangerous signal may be provided to the operator using a vibrating motor, and mechanism for operating the clutch module 60 is applied to enhance the operation of the clutch.

In addition, for the rotation motion of the needle 110 with two degree of freedom or the plane motion of the needle 110 with two degree of freedom, belt-pulley mechanism and a connection between a driver and a brake are simplified, and friction force and driving force or fixing force may be properly provided to operate the interventional procedure.

In addition, the friction force generated from the master device in the rotational motion of the needle 110 with two degrees of freedom may be controlled or prevented. The slave robot 130 may be smoothly rotated along the first rotational direction with respect to the first rotational axis 31a, the second rotational direction with respect to the second rotational axis 32a, and the mixed rotational direction crossing the first and second rotational directions.

In addition, the haptic feedback may be performed for the plane motion of the needle 110 with two degrees of freedom and the linear motion of the needle 110 with one degrees of freedom, to protect the patient from the needle 110.

In addition, the reaction force may be provided corresponding to the motion of the needle 110 with each degree of freedom and the needle 110 may be stopped at the predetermined cautious area.

In addition, the needle 110 may be prevented from damaging the human body at the predetermined cautious area, to protect the patient in the interventional procedure and to protect the medical accident.

In addition, the rotational motion module 30 is not operated with the linear motion mode or the plane motion mode, and quantity of motion of the rotational motion module 30 may be accurately detected for the rotational motion of the gripper 10 with two degrees of freedom.

In addition, the linear motion with one degree of freedom, the rotational motion with two degrees of freedom, and the plane motion with two degrees of freedom may be clearly discriminated, the needle 110 may be precisely controlled for each motion, and the position of the needle 110 may be accurately and precisely controlled.

In addition, each motion may be stably provided to the needle driver 120 and the slave robot 130, and thus negligent accident due to the malfunction of the mode selection may be prevented.

In addition, using the master device for the interventional procedure, the needle 110 may be automatically inserted into the human body, and the operator may be prevented from being exposed to radiation. In addition, as five degrees of freedom of the needle 110, the linear motion with one degree of freedom, the rotational motion with two degrees of freedom and the plane motion with two degrees of freedom may be selectively performed, so that the needle 110 may be inserted into the human body more accurately, the needle 110 may be prevented to be vibrated due to the operation of the master device in the inserting into the human body, and the selected motion mode may be only performed without intervening the other motion modes, in controlling the master device.

In addition, the motion of the needle 110 may be enlarged, the degree of freedom of the needle 110 may be also enlarged, and the rotation motion with two degrees of freedom and the plane motion with two degrees of freedom may be limited to prevent the vibration of the needle 110, and thus the needle 110 may be inserted more stably and more accurately.

In addition, the interface for the master device for the interventional procedure may be simplified in using the master device 100, and the needle inserting type remote control interventional procedure and the processes thereof may be more optimized.

In addition, the driving input and the reaction force may be freely performed for each motion, each motion of the needle 110 may be separated, each motion mode may be clearly discriminated for each separated motion, and further each individual operation may be easily performed at each motion mode.

Although the exemplary embodiments of the present invention have been described, it is understood that the present invention should not be limited to these exemplary embodiments but various changes and modifications can be made by one ordinary skilled in the art within the spirit and scope of the present invention as hereinafter claimed.

What is claimed is:

1. A handle unit for interventional procedure, the handle unit being gripped by an operator corresponding to movement of a needle for the interventional procedure, the handle unit comprising:
    a gripper adapted to be gripped by the operator;
    a mode selection module equipped to the gripper, and configured to select one of motion modes comprising a linear motion mode, a rotational motion mode and a plane motion mode, the needle linearly moving with one degree of freedom in the linear motion mode, the needle rotationally moving with two degrees of freedom in the rotational motion mode, the needle moving in a plane with two degrees of freedom in the plane motion mode; and
    a linear motion module equipped to the gripper, and configured to perform a linear motion of the needle based on a selection of the mode selection module,
    wherein a moving direction of the needle by the linear motion module is different from an extending direction of the plane in which the plane motion mode is performed.

2. The handle unit of claim 1, wherein the linear motion module comprises:
    an inserting guider combined with an inside of the gripper, a guiding rail longitudinally extending in a longitudinal direction of the inserting guider;
    an inserting shaft combined with the inserting guider at a side of the guiding rail and configured to move back and forth in the inserting guider;
    a linear motion sensor configured to sense a position of the inserting shaft;
    a combining block slidably combined with the guiding rail and the inserting shaft, and connected to the linear motion sensor; and
    a returning elastic part equipped to the guiding rail, and configured to return the combining block to an initial position.

3. The handle unit of claim 2, wherein the linear motion module further comprises a guiding plate, which is combined with the linear motion sensor and the gripper, and supports the combining block to move.

4. The handle unit of claim 1, wherein the gripper comprises:
    a linear body having the linear motion module inside thereof and adapted to be gripped by the operator;
    a control body protruded at a first side of the linear body to form a first sectional area larger than that of the linear body, having the mode selection module, and exposing a control lever controlling the linear motion module; and
    a support body protruded at a second side of the linear body to form a second sectional area larger than that of the linear body.

5. The handle unit of claim 1, further comprising:
    a haptic generating module configured to vibrate the gripper or the linear motion module.

6. A master device for interventional procedure, the master device comprising:
    the handle unit as claimed in claim 1;
    a rotational motion module configured to rotate the needle based on a selection of the rotational motion mode, and combined with the gripper; and
    a plane motion module configured to move the needle in a plane based on a selection of the plane motion mode, and combined with the rotational motion module.

7. The master device of claim 6, wherein the handle unit further comprises:
    a clutch module configured to determine an operation of one of the linear motion module, the rotational motion module and the plane motion module, corresponding to the one of the motion modes selected by the mode selection module.

8. The master device of claim 6, wherein the rotational motion module further comprises:
    a first rotation base combined with the plane motion module;
    a second rotation base combined with the first rotation base to be rotated with a first rotational axis;
    a gripper combiner combined with the gripper, and combined with the second rotation base to be rotated with a second rotational axis crossing the first rotational axis;
    a first rotation driver equipped to the first rotation base, and configured to provide a first rotational reaction force to the second rotation base; and
    a second rotation driver equipped to the second rotation base, and configured to provide a second rotational reaction force to the gripper combiner.

9. The master device of claim 8, wherein the rotational motion module further comprises:
    a first absolute angle detector equipped to the first rotational axis, and configured to detect a rotational state of the second rotation base; and
    a second absolute angle detector equipped to the second rotational axis, and configured to detect a rotational state of the gripper combiner,
    wherein a rotational motion of the needle is performed based on detection of the first absolute angle detector and detection of the second absolute angle detector,
    wherein the first rotation driver and the second rotation driver are respectively operated based on the detection of the first absolute angle detector and the detection of the second absolute angle detector, with a start signal starting the rotational motion of the needle or an end signal finishing the rotational motion of the needle, for returning the handle unit to be a neutral position.

10. The master device of claim 8, wherein the rotational motion module further comprises:
  a weight balancer configured to maintain a weight balance between the first rotation base and the second rotation base.

11. The master device of claim 8, wherein the plane motion module comprises:
  a first plane base;
  a second plane base spaced apart from the first plane base;
  a first centering block slidably combined with the first plane base along a first plane direction, combined with the second plane base; and
  a second centering block slidably combined with the second plane base along a second plane direction crossing the first plane direction, combined with the rotational motion module.

12. The master device of claim 11, wherein the plane motion module further comprises:
  a first plane motion detector configured to detect a moving state of the first centering block with respect to the first plane base; and
  a second plane motion detector configured to detect a moving state of the second centering block with respect to the second plane base,
  wherein a rotational motion of the needle is performed based on detection of the first plane motion detector and detection of the second plane motion detector,
  wherein the first rotation driver and the second rotation driver are respectively operated based on the detection of the first plane motion detector and the detection of the second plane motion detector, with a start signal starting the rotational motion of the needle or an end signal finishing the rotational motion of the needle, for returning the handle unit to be a neutral position.

13. A remote control interventional procedure system operating a needle with five degrees of freedom, the system comprising:
  the master device as claimed in claim 6;
  a needle driver configured to linearly move the needle based on an operation of the linear motion module;
  a slave robot configured to rotationally move the needle based on an operation of the rotational motion module, or move the needle in a plane based on an operation of the plane motion module; and
  an interventional control unit configured to control the needle driver and the slave robot based on an operation of the master device.

* * * * *